United States Patent
Chang et al.

(10) Patent No.: US 6,680,306 B2
(45) Date of Patent: Jan. 20, 2004

(54) METHOD FOR ENHANCING THE EFFECTIVENESS OF CANCER THERAPIES

(75) Inventors: Yan Chang, Ashland, MA (US); Vodek Sasak, Northboro, MA (US)

(73) Assignee: GlycoGenesys, Inc., Boston, MA (US)

( * ) Notice: Subject to any disclaimer, the term of this patent is extended or adjusted under 35 U.S.C. 154(b) by 0 days.

(21) Appl. No.: 10/176,235

(22) Filed: Jun. 20, 2002

(65) Prior Publication Data

US 2003/0013681 A1 Jan. 16, 2003

Related U.S. Application Data

(60) Provisional application No. 60/299,991, filed on Jun. 21, 2001.

(51) Int. Cl.$^7$ .................. A61K 31/715; C08B 37/06
(52) U.S. Cl. ...................... 514/54; 514/53; 514/61; 514/62; 536/2; 536/123.1
(58) Field of Search .................. 514/53, 54, 61, 514/62; 536/2, 123.1

(56) References Cited

U.S. PATENT DOCUMENTS

| | | | |
|---|---|---|---|
| 5,490,991 A | 2/1996 | Enriquez et al. | 424/488 |
| 5,681,923 A | 10/1997 | Platt | 530/300 |
| 5,843,442 A | 12/1998 | Soule et al. | 424/145.1 |
| 5,895,784 A | 4/1999 | Raz et al. | 514/54 |
| 6,423,314 B2 | 7/2002 | Platt | 424/184.1 |
| 6,500,807 B1 * | 12/2002 | Platt et al. | 514/44 |
| 2002/0107222 A1 | 8/2002 | Platt | |

OTHER PUBLICATIONS

Inohara, H. et al. Effects of Natural Complex Carbohydrate (Citrus Pectin) on Murine Melanoma Cell Properties Related to Galectin–3 Functions. Glycoconjugate Journal 1994, 11, 527–32.*

GBC 590 SafeScience Clinical Data. R7D Focus Drug News (Apr. 2, 2001), AN 2001:1186 DRUGNL.*

"Galectin–3 mediates genistein–induced G2/M arrest and inhibits apoptosis" Huei–Min Lin et al. Carcinogenesis 2000 21(11):1941–1945.

"Cell Cycle Arrest and Inhibition of Anoikis by Galectin–3 in Human Breast Epithelial Cells" Hyeong–Reh Choi Kim et al. Cancer Research Aug. 15, 1999 59:4148–4154.

"Galectin–3 Induces Endothelial Cell Morphogenesis and Angiogenesis" Pratima Nangia–Makker et al. American Journal of Pathology, Mar. 2000, 156(3):899–909.

"Rapid Release of Intracellular Galectin–3 from Breast Carcinoma Cells by Fetuin" Wen–Qin Zhu et al. Cancer Research, Mar. 1, 2001, 61:1869–1873.

"Effects of Thomsen–Friedenreich Antigen–specific Peptide P–30 on B–Galactoside–mediated Homotypic Aggregation and Adhesion to the Endothelium of MDA–MB–435 Human Breast Carcinoma Cells" Vladislav V. Glinsky et al. Cancer Research, May 15, 2000, 60:2584–2588.

"The Role of Thomsen–Friedenreich Antigen in Adhesion of Human Breast and Prostate Cancer Cells to the Endothelium" Vladislav V. Glinsky et al. Cancer Research, Jun. 15, 2001, 61:4851–4857.

"Cell Cycle Arrest and Inhibition of Anoikis by Galectin–3 in Human Breast Epithelial Cells" Hyeong–Reh Choi Kim et al. Cancer Research, Aug. 15, 1999, 59:4148–4154.

The NH2 Terminus of Galectin–3 Governs Cellular Compartmentalization and Functions in Cancer Cells Hua Chang Gong et al. Cancer Research, Dec. 15, 1999, 59:6239–6245.

"Comparative Analysis of Galectins in Primary Tumors and Tumor Metastasis in Human Pancreatic Cancer" Pascal O. Berberat et al. The Journal of Histochemistry & Cytochemistry, 2001 49(4):539–549.

"Concentrations of Galectin–3 in the Sera of Normal Controls and Cancer Patients" Ida Iurisci et al. Clinical Cancer Research, Apr. 2000, 6:1389–1393.

"Phosphorylation of the B–Galactoside–binding Protein Galectin–3 Modulates Binding to Its Ligands" Nachman Mazurek et al. The Journal of Biological Chemistry, Nov. 17, 2000, 275(46):36311–36315.

"Increased Galectin–3 Expression in Gastric Cancer: Correlations with Histopahtological Subtypes, Galactosylated Antigens and Tumor Cell Proliferation" S.E. Baldus et al. Tumor Biol., 2000, 21:258–266.

"Galectin–3 overexpression protects from apoptosis by improving cell adhesion properties" (Abstract) Matarrese et al., Int. J. Cancer, Feb. 15, 2000, 85(4):545–54.

Rabinovich G.A. et al. "Galectins and their ligands: amplifiers, silencers or tuners of the inflammatory response?" Trends in Immunology, vol. 23, No. 6, pp. 313–320 (Jun. 2002).

Pienta, K.J. et al. Inhibition of Spontaneous Metastasis in a Rat Prostate Cancer Model by Oral Administration of Modified Citrus Pectin. J. Nat. Cancer Inst. 87, 348–353 (Mar. 1, 1995).

Platt, D. and Raz, A. Modulation of the lung Colonization of B16–F1 Melanoma Cells by Citrus Pectin. J. Nat. Cancer Inst. 84, 438–442 (Mar. 18, 1992).

* cited by examiner

Primary Examiner—Kathleen K. Fonda
(74) Attorney, Agent, or Firm—Ropes & Gray LLP

(57) ABSTRACT

The efficacy of conventional cancer therapies such as surgery, chemotherapy and radiation is enhanced by the use of a therapeutic material which binds to and interacts with galectins. The therapeutic material can enhance apoptosis thereby increasing the effectiveness of oncolytic agents. It can also inhibit angiogenesis thereby moderating tumor growth and/or metastasis.

23 Claims, No Drawings

METHOD FOR ENHANCING THE EFFECTIVENESS OF CANCER THERAPIES

RELATED APPLICATION

This patent application claims priority of U.S. Provisional Patent Application Serial No. 60/299,991 filed Jun. 21, 2001, and entitled "Method for Enhancing the Effectiveness of Cancer Therapies."

FIELD OF THE INVENTION

This invention relates generally to methods and materials for the treatment of cancer. More specifically, the invention relates to methods and materials for enhancing the effectiveness of cancer therapies.

BACKGROUND OF THE INVENTION

Conventional treatment for cancers involves the use of chemotherapeutic agents, radiation, and surgery, either alone or in combination. The medical arts have developed a number of treatments based upon the foregoing therapies. The present invention is directed to specific materials which can act to enhance the effectiveness of the foregoing therapies.

Galectins comprise a family of proteins which are expressed by plant and animal cells and which bind β-galactoside sugars. These proteins can be found on cell surfaces, in cytoplasm, and in extracellular fluids. They have a molecular weight in the general range of 29–34 kD; they have an affinity for β-galactoside containing materials, and have been found to play a number of important roles in biological processes including cell migration, cell-cell adhesion, angiogenesis, cell fusion and other cell-cell interactions, as well as immune-based reactions and apoptosis. As such, the role of galectins is very strongly tied to cancer and other proliferative diseases. While there are a large number of galectins which manifest the foregoing activities, galectin-3 and galectin-1 have been strongly implicated in connection with cellular processes involving cancers.

Galectin-3 is a carbohydrate binding protein having a molecular weight of approximately 30,000. It is composed of two distinct structural motifs, an amino-terminal portion containing Gly-X-Y tandem repeats which are characteristic of collagens, and a carboxyl-terminal portion containing a carbohydrate binding site. Galectin-3 is found in almost all tumors, and has a binding affinity for β-galactoside-containing glyco-conjugates. Galectin-3 is believed to play a role in mediating cell-cell interactions and thereby fostering metastasis. It has been found that cells which have high expressions of galectin-3 are more prone to metastasis and are more resistant to apoptosis induced by chemotherapy or radiation. It has also been reported in the literature that galectin-3 plays a role in promoting angiogenesis.

Galectin-1 is a highly conserved homodimer of 14–15 kD and is one of the most abundant of the galectins. It binds to laminin which has been found to exert strong regulatory effects on cellular interactions such as adhesion, proliferation, migration and differentiation. In this regard, galectin-1 has been found to strongly influence these processes in various cells. It is believed to be implicated in the secretion of a number of cellular growth factors and interleukins. Galectin-1 has been found to be expressed at very high levels in many cancer cells and is strongly implicated in metastasis.

In accord with the present invention, it has been found that certain therapeutic materials can bind to galectins thereby inactivating them toward interaction with other carbohydrate materials and/or cells. Specifically, it has been found that treatment of galectin bearing cells with the therapeutic materials of this invention can inhibit the interaction of those cells with other cells and/or biomolecules and thereby inhibit angiogenesis and enhance the efficacy of apoptosis-inducing therapies such as chemotherapy or radiation. Furthermore, these materials can inhibit cell-cell interactions and thereby enhance the effectiveness of surgical therapies by inhibiting metastases, which are often initiated by surgical dislodgement of cells.

As will be explained in detail hereinbelow, the materials of the present invention are generally comprised of natural or synthetic polymers and oligomers. They are very low in toxicity and interact synergistically with heretofore employed cancer therapies so as to increase the effectiveness thereof. Through the use of the present invention, the dosages of potentially toxic therapies such as chemotherapies and radiation may be reduced. Likewise, the effectiveness of surgical therapies is enhanced by the use of the present invention. For example, since the methodology of the present invention acts to inhibit the post-surgery metastatic process, use of this invention allows a surgeon to implement more aggressive surgical therapies without being limited by the possibility of precipitating metastatic events. These and other advantages of the invention will be discussed hereinbelow.

BRIEF DESCRIPTION OF THE INVENTION

There is disclosed herein a method for enhancing the efficacy of a therapeutic treatment for cancer in a patient. The treatment being enhanced may comprise chemotherapy, radiation therapy, surgery and combinations thereof. The method of the present invention comprises administering to a patient a therapeutically effective amount of a compound which binds to a galectin. This compound may be administered prior to, after, or concomitant with the other treatment.

A preferred class of therapeutic materials of the present invention comprises a polymeric backbone having side chains dependent therefrom. The side chains are terminated by a galactose or arabinose unit. This material may be synthetic, natural, or semi-synthetic. In one particular embodiment, the therapeutic compound comprises a substantially demethoxylated polygalacturonic acid backbone which is interrupted with rhamnose residues.

In general, the materials of the present invention have a molecular weight in excess of 300 dalton. One specific group of materials has a molecular weight in the range of 300 to 2,000 daltons. In those instances where the materials of the present invention are based upon complex carbohydrates such as pectins, a preferred group of materials has a molecular weight in the range of 1–50 kilodalton. The therapeutic materials of the present invention may be administered orally, by injection, transdermally, or by topical application, depending upon the specific type of cancer being treated, and the adjunct therapy.

DETAILED DESCRIPTION OF THE INVENTION

The present invention recognizes that the effectiveness of conventional cancer therapies such as chemotherapy, surgery and radiation can be enhanced through the use of a therapeutic material which interacts with galectins.

While galectins are known to bind galactose and other such simple sugars in vitro, those simple sugars are not therapeutically effective in moderating galectin mediated cellular processes in vivo. While not wishing to be bound by speculation, the inventors hereof presume that relatively small sugar molecules are incapable of sustainably blocking, activating, suppressing, or otherwise interacting with other portions of the galectin protein. Therefore, preferred materials for the practice of the present invention generally comprise molecules which contain an active galectin binding sugar site, but which have somewhat higher molecular weights than simple sugars. Such molecules preferably have a minimum molecular weight of at least 300 daltons, and most typically a minimum molecular weight in the range of 300–2,000 daltons. Some specifically preferred materials have yet higher molecular weight ranges. A preferred class of therapeutic materials comprises oligomeric or polymeric species having one or more sugars such as galactose or arabinose pendent therefrom. The oligomeric or polymeric backbone may be synthetic or organic. Materials of this type are disclosed in U.S. patent No. (EX Ser. No. 09/750,726) the disclosure of which is incorporated herein by reference. Such materials will preferably have a molecular weight in the range of 300–50,000 daltons and one particular material comprises a cellulose backbone with galactose terminated side chains pendent therefrom. It should be kept in mind that there is some inherent uncertainty in molecular weight measurements of high molecular weight carbohydrates, and measured molecular weights will be somewhat dependent on the method used for measuring the molecular weight. Molecular weights given herein are based on viscosity measurements, and such techniques are known in the art.

One group of materials falling within this general class comprises a substantially demethoxylated polygalacturonic acid backbone having rhamnose residues pendent therefrom. It is believed that in materials of this type, the terminal galactose or arabinose units pendent from the backbone bind to galectin proteins. The remaining bulk of the molecule potentiates the compound's action in moderating immune system response; and as discussed hereinabove, the inventors, while not wishing to be bound by speculation, believe that the remaining bulk of the molecule either interacts with remaining portions of the galectin protein and/or prolongs the binding of the sugar portion thereto. Materials of this general type are described by formulas I, II and III hereinbelow, and it is to be understood that yet other variants of this general compound may be prepared and utilized in accord with the principles of the present invention.

(I)

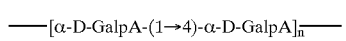

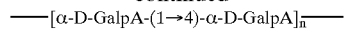

where $n \geq 1$.

(II)

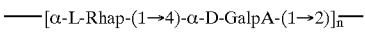

where $n \geq 1$.

(III)

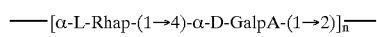

where $n \geq 1$.

Pectin is a complex carbohydrate having a highly branched structure comprised of a polygalacturonic backbone with numerous branching side chains dependent therefrom. The branching creates regions which are characterized as being "smooth" and "hairy." It has been found that pectin can be modified by various chemical, enzymatic or physical treatments to break the molecule into smaller portions having a more linearized, substantially demethoxylated polygalacturonic backbone with pendent side chains of rhamnose residues having decreased branching. This material is known in the art as modified pectin, and its efficacy in treating cancer has been established; although galectin blocker materials of this type have not been used in conjunction with surgery, chemotherapy or radiation.

U.S. Pat. No. 5,895,784, the disclosure of which is incorporated herein by reference, describes modified pectin materials, techniques for their preparation, and use of the material as a treatment for various cancers. The material of the '784 patent is described as being prepared by a pH based modification procedure in which the pectin is put into solution and exposed to a series of programmed changes in pH which results in the breakdown of the molecule to yield therapeutically effective modified pectin. The material in the '784 patent is most preferably prepared from citrus pectin; although, it is to be understood that modified pectins may be prepared from pectin starting material obtained from other sources, such as apple pectin and the like. Also, modification processes may be accomplished by enzymatic treatment of the pectin, or by physical processes such as heating. Further disclosure of modified pectins and techniques for their preparation and use are also disclosed in U.S. Pat. No. 5,834,442 and U.S. patent application Ser. No. 08/024,487, the disclosures of which are incorporated herein by reference. Modified pectins of this type generally have molecular weights in the range of 1–50 kilodalton, and a preferred group of such materials has an average molecular weight in the range of 1–15 kilodalton, with a specific group of materials having a molecular weight of about 10 kilodalton.

As disclosed in the prior art, such modified pectin materials have therapeutic efficacy against a variety of cancers. These materials interact with galectins, including galectin-1 and galectin-3, and in that regard also have efficacy against immune based diseases. In accord with the present invention, the effect of conventional cancer therapies is enhanced by use of pectin materials and other materials which interact with galectins. These materials may be administered orally; or by intravenous injection; or by injection directly into an affected tissue, as for example by injection into a tumor site. In some instances the materials may be applied topically at the time surgery is carried out. Also, other techniques such as transdermal delivery systems, inhalation, subcutaneous implantation, or the like may be employed.

Radiation therapy for cancer, which includes gamma radiation as well as particle beams, and oncolytic chemotherapeutic agents are cytotoxic, and their effectiveness in treating cancer is based upon the fact that cancerous cells are generally more sensitive to such cytotoxic therapies than are normal cells either because of their rapid metabolism, or because they employ biochemical pathways not employed by normal cells. It is believed that these therapies exert their cytotoxic effects by activating programmed cell death, also referred to as apoptosis. Cells undergo apoptosis when they undergo a critical level of damage. A balance between the activities of apoptotic and anti-apoptotic intracellular signal transduction pathways is important toward a cell's decision of whether to undergo apoptosis or to attempt internal repair. It has been demonstrated that galectins, and specifically galectin-3, are involved in both apoptosis resistance and tumor progression.

Galectin-3 has been implicated in inhibiting apoptosis in cells treated with oncolytic agents such as cisplatin, genistein and the like. It was found that genistein effectively induces apoptosis, without detectable cell cycle arrest, in BT549 cells, which comprise a human breast epithelial cell line that does not express detectable levels of galectin-3. However, when galectin-3 transfected BT549 cells are treated with genistein, cell cycle arrest at the G(2)/M phase takes place without apoptosis induction (Lin et al. Galectin-3 mediates genistein-induced G(2)/M arrest and inhibits apoptosis. *Carcinogenesis* 2000 Nov.; 21(11):1941–5). It was also found that although BT549 cells undergo anoikis, galectin-3 overexpressing BT549 cells respond to the loss of cell adhesion induced by G1 arrest without detectable cell death. Studies also suggest that galectin-3 is a critical determinant for anchorage-independent cell survival of disseminating cancer cells in the circulation during metastasis. (Kim et al. Cell cycle arrest and inhibition of anoikis by galectin-3 in human breast epithelial cells. *Cancer Res.* 1999 August 15; 59(16):4148–54).

Galectin-3 has also been shown to protect cells from apoptosis by moderating cell-cell and cell-matrix interaction, and has been shown to be involved in tumor progression and metastasis. When galectin-3 transfected human breast cancer cells are compared with their parent cell line which do not express galectin-3, it is found that the overexpressing cells: (1) had a significantly enhanced adhesion to laminin, fibronectin and vitronectin exerted both directly and/or via increased expression of specific integrins; the cells also exhibited (2) a remodeling of those cytoskeletal elements associated with cell spreading, i.e. microfilaments; and (3) enhanced survival upon exposure to different apoptotic stimuli such as cytokine and radiation (Matarrese et al. Galectin-3 overexpression protects from apoptosis by improving cell adhesion properties. *Int. J Cancer* 2000 February 15; 85(4):545–54).

The role of galectins in promoting angiogenesis has also been shown. It is known that in order for a primary tumor to grow or metastasize the cell must release chemical information instructing endothelial cells to form blood vessels which nourish and support the tumor cell. Galectins have also proven to be involved in the processes of metastasis and angiogenesis. It is shown that galectin-3 affects chemotaxis and morphology, and stimulates capillary tube formation of IIUV-EC-C in vitro and angiogenesis in vivo. Endothelial cell morphogenesis is a carbohydrate-dependent process which is neutralized by specific sugars and antibodies. These findings demonstrate that endothelial cell surface carbohydrate recognition events can induce a signaling cascade leading to the differentiation and angiogenesis of endothelial cells (Nangia-Makker et al. Galectin-3 induces endothelial cell morphogenesis and angiogenesis. *Am. J Pathol.* 2000 March; 156(3):899–909). The materials of the present invention have been demonstrated to interact with galectins and inhibit angiogenesis.

Clearly, galectins in general and galectin-3 in particular have been demonstrated to have diverse and very significant effects on the growth and proliferation of cancer cells. Furthermore, compounds which block or neutralize the activity of galectins inhibit angiogenesis and promote apoptosis. Therefore, such material will beneficially enhance the effects of oncolytic therapies. Also, it has been demonstrated that such materials will strongly inhibit angiogenesis and/or metastasis; therefore, these materials will prevent or minimize metastatic events induced by surgical disruption of a tumor site.

In accord with the present invention, a galectin binding therapeutic material is administered to a patient, in combination with conventional therapies such as surgery, radiation or chemotherapy. The material is most preferably administered prior to the administration of the conventional therapy, so as to allow it sufficient time to interact with and bind to galectins in the tumor or in non-cancerous cells. Depending on the nature of the cancer and the therapy, administration of the galectin binding therapeutic material may be continued while the other therapy is being administered and/or thereafter. Administration of the galectin binding material may be made in a single dose, or in multiple doses. In some instances, administration of the therapeutic material is commenced at least several days prior to the conventional therapy, while in other instances, administration is begun either immediately before or at the time of the administration of the conventional therapy. In some instances, particularly with regard to surgical therapies, the carbohydrate material may be advantageously administered both before, during and after the therapy.

The foregoing discussion has been primary directed toward modified pectin materials and materials which interact with galectins-1 and 3; however, it is to be understood that other galectins are also known to be involved in the progress of various cancers, and both the modified pectin material as well as the other therapeutic materials discussed hereinabove interact with galectins. Therefore, other materials and methods may be employed in the practice of the present invention. The foregoing discussion and description is illustrative of specific embodiments, but is not meant to be a limitation upon the practice thereof. It is the following claims, including all equivalents, which define the scope of the invention.

What is claimed is:

1. A method for enhancing the efficacy of an oncolytic chemotherapeutic in a patient, said method comprising administering to said patient, prior to or concomitant with said oncolytic chemotherapeutic, a therapeutically effective amount of a carbohydrate that binds to a galectin; and administering said oncolytic chemotherapeutic to said patient.

2. A method for enhancing the efficacy of a surgical treatment for cancer in a patient, said method comprising administering surgery to said patient; and administering to said patient, a therapeutically effective amount of a carbohydrate that binds to a galectin, whereby the efficacy of said surgery is enhanced.

3. The method of claim 1 or 2 wherein said carbohydrate binds to galectin-1 or galectin-3.

4. The method of claim 1 or 2, wherein said carbohydrate comprises a polymeric backbone having side chains dependent therefrom, said side chains being terminated by a galactose or arabinose unit.

5. The method of claim 1 or 2, wherein said carbohydrate comprises a substantially demethoxylated polygalacturonic acid which is interrupted with rhamnose residues.

6. The method of claim 1 or 2, wherein said carbohydrate comprises a branched carbohydrate.

7. The method of claim 1 or 2, wherein said carbohydrate comprises a modified pectin.

8. The method of claim 7, wherein said modified pectin comprises a pH modified pectin.

9. The method of claim 8, wherein said modified pectin comprises an enzymatically modified pectin.

10. The method of claim 7, wherein said modified pectin comprises a thermally modified pectin.

11. The method of claim 7, wherein said modified pectin comprises a modified citrus pectin.

12. The method of claim 1 or 2, wherein said carbohydrate has a molecular weight of at least 300 dalton.

13. The method of claim 1 or 2, wherein said carbohydrate has a molecular weight in the range of 300–2,000 dalton.

14. The method of claim 7, wherein said modified pectin has molecular weight in the range of 1–50 kilodalton.

15. The method of claim 7, wherein said modified pectin has a molecular weight in the range of 1–15.

16. The method of claim 7, wherein said modified pectin has molecular weight of approximately 10 kilodalton.

17. The method of claim 1 or 2, wherein administering said carbohydrate to said patient comprises injecting said carbohydrate into said patient.

18. The method of claim 1 or 2, wherein administering said carbohydrate to said patient comprises orally administering said carbohydrate to said patient.

19. The method of claim 1, wherein administering said carbohydrate to said patient comprises administering said carbohydrate prior to administering said oncolytic chemotherapeutic to said patient.

20. The method of claim 1, wherein said carbohydrate is administered concomitant with said oncolytic chemotherapeutic.

21. The method of claim 1, further comprising administering said carbohydrate following said oncolytic chemotherapeutic.

22. The method of claim 2, wherein administering said carbohydrate to said patient comprises administering said carbohydrate prior to administering said surgery.

23. The method of claim 2, wherein said carbohydrate is administered concomitant with said surgery.

* * * * *

UNITED STATES PATENT AND TRADEMARK OFFICE
CERTIFICATE OF CORRECTION

PATENT NO.     : 6,680,306 B2
DATED          : January 20, 2004
INVENTOR(S)    : Yan Chang et al.

It is certified that error appears in the above-identified patent and that said Letters Patent is hereby corrected as shown below:

Column 8,
Line 10, after "has" insert -- a --;
Line 11, change "whereinsaid" to -- wherein said --; and
Line 12, after "15" insert -- kilodalton --.

Signed and Sealed this

Twentieth Day of April, 2004

JON W. DUDAS
*Acting Director of the United States Patent and Trademark Office*

(12) INTER PARTES REEXAMINATION CERTIFICATE (0215th)
United States Patent
Chang et al.

(10) Number: US 6,680,306 C1
(45) Certificate Issued: Dec. 7, 2010

(54) METHOD FOR ENHANCING THE EFFECTIVENESS OF CANCER THERAPIES

(75) Inventors: Yan Chang, Ashland, MA (US); Vodek Sasak, Northboro, MA (US)

(73) Assignee: Glycogenesys, Inc., Boston, MA (US)

Reexamination Request:
No. 95/000,074, Jan. 31, 2005

Reexamination Certificate for:
| | |
|---|---|
| Patent No.: | 6,680,306 |
| Issued: | Jan. 20, 2004 |
| Appl. No.: | 10/176,235 |
| Filed: | Jun. 20, 2002 |

Certificate of Correction issued Apr. 20, 2004.

Related U.S. Application Data

(60) Provisional application No. 60/299,991, filed on Jun. 21, 2001.

(51) Int. Cl.
| | |
|---|---|
| *A61K 45/06* | (2006.01) |
| *A61K 31/732* | (2006.01) |
| *A61K 45/00* | (2006.01) |
| *A61K 31/00* | (2006.01) |

(52) U.S. Cl. ............................. 514/54; 514/53; 514/61; 514/62; 536/123.1; 536/2

(58) Field of Classification Search .................... 514/53, 514/54, 61, 62
See application file for complete search history.

(56) References Cited

U.S. PATENT DOCUMENTS

| | | | | |
|---|---|---|---|---|
| 5,490,991 A | | 2/1996 | Enriquez et al. | |
| 5,498,702 A | * | 3/1996 | Mitchell et al. | ................. 536/2 |
| 5,547,945 A | | 8/1996 | Ye et al. | |
| 5,639,737 A | | 6/1997 | Rubin | |
| 5,681,923 A | | 10/1997 | Platt | |
| 5,831,052 A | | 11/1998 | Hillman et al. | |
| 5,834,442 A | * | 11/1998 | Raz et al. | ...................... 514/54 |
| 5,895,784 A | | 4/1999 | Raz et al. | |
| 6,258,383 B1 | | 7/2001 | Gohlke et al. | |
| 6,274,566 B1 | * | 8/2001 | Eliaz et al. | .................... 514/54 |
| 6,423,314 B2 | | 7/2002 | Platt | |
| 6,482,806 B1 | * | 11/2002 | Koyama et al. | ................ 514/54 |
| 6,500,807 B1 | | 12/2002 | Platt et al. | |
| 6,642,205 B2 | | 11/2003 | Klyosov et al. | |
| 6,645,946 B1 | | 11/2003 | Klyosov et al. | |
| 6,680,306 B2 | | 1/2004 | Chang et al. | |
| 6,875,451 B2 | | 4/2005 | Ellison et al. | |
| 6,914,055 B2 | * | 7/2005 | Klyosov et al. | ................ 514/54 |
| 6,982,255 B2 | * | 1/2006 | Klyosov et al. | ................ 514/54 |
| 7,012,068 B2 | * | 3/2006 | Klyosov et al. | ................ 514/54 |
| 2002/0107222 A1 | | 8/2002 | Platt | |
| 2003/0013681 A1 | | 1/2003 | Chang et al. | |
| 2003/0064957 A1 | | 4/2003 | Klyosov et al. | |

FOREIGN PATENT DOCUMENTS

| | | |
|---|---|---|
| EP | 0 888 776 A1 | 1/1999 |
| JP | 7-109226 | 4/1995 |
| WO | WO 97/00527 * | 9/1997 |
| WO | WO-97/34907 | 9/1997 |
| WO | WO 97/34907 * | 9/1997 |
| WO | WO-00/07624 | 2/2000 |
| WO | WO-00/62076 | 10/2000 |
| WO | WO-02/26262 | 4/2002 |
| WO | WO-02/057284 | 7/2002 |
| WO | WO-02/076474 | 10/2002 |

OTHER PUBLICATIONS

Pienta, K. et al "Phase II evaluation of oral estramustine and oral etoposide . . . " J. Clin. Oncol. (1994) vol. 12, No. 10, pp. 2005–2012.*

Kidd, P. "A new approach to mestastatic cancer prevention . . . " Alt. Med. Rev. (1996) vol. 1, No. 1, pp. 4–10.*

Ducreaux, M. et al "Irinotecan combined with bolus fluorouracil . . . " J. Clin. Oncol. (1999) vol. 17, pp. 2901–2908.*

Guess et al., "Modified Citrus Pectin (MCP) Increases the Prostate–Specific Antigen Doubling Time in Men with Prostate Cancer: A Phase II Pilot Study," Prostate Cancer and Prostatic Diseases 6:301–304 (2003).

Hayashi et al., "Effects of Daily Oral Administration of Quercetin Chalcone and Modified Citrus Pectin on Implanted Colon–25 Tumor Growth in Balb–c Mice," Alternative Medicine Review 5(6):546–552 (2000).

Liu et al., "Citrus Pectin: Characterization and Inhibitory Effect on Fibroblast Growth Factor—Receptor Interaction," J. Agric. Food Chem. 49:3051–3057 (2001).

Nangia–Makker et al., "Galectin–3 Induces Endothelial Cell Morphogenesis and Angiogenesis," American Journal of Pathology 156(3):899–909 (2000).

Nangia–Makker et al., "Inhibition of Human Cancer Cell Growth and Metastasis in Nude Mice by Oral Intake of Modified Citrus Pectin," Journal of the National Cancer Institute 94(24):1854–1862 (2002).

Takenaka et al., "Galectin–3 and Metastasis," Glyococonjugate Journal 19:543–549 (2004).

D. Platt et al. Modulation of the Lung Colonization of B16–F1 Melanoma Cells by Citrus Pectin. J. of Nat. Cancer Inst. 84(6), Mar. 18, 1992, pp. 438–442.

G. V. Glinsky et al. Inhibition of Human Breast Cancer Metastasis in Nude Mice by Synthetic Glycoamines. Cancer Research 56, Dec. 1, 1996, pp. 5319–5324.

G. V. Glinsky et al. Inhibition of colony formation in agarose of metastatic human breast carcinoma etc. Clin. & Exp. Metastasis 14(3), 1996, pp. 253–267.

G. V. Glinsky. Anti–adhesion cancer therapy. Cancer & Metast. Rev. 17 (1998) pp. 177–185.

(Continued)

*Primary Examiner*—Padmashri Ponnaluri

(57) ABSTRACT

The efficacy of conventional cancer therapies such as surgery, chemotherapy and radiation is enhanced by the use of a therapeutic material which binds to and interacts with galectins. The therapeutic material can enhance apoptosis thereby increasing the effectiveness of oncolytic agents. It can also inhibit angiogenesis thereby moderating tumor growth and/or metastasis.

OTHER PUBLICATIONS

S. K. Green et al. Adhesion–dependent multicellular drug resistance. Anti–Cancer Drug Design 14 (1999) pp. 153–168.

A. Frankel et al. Synthetic glycoamine analogs synergize with taxol and cisplatin etc. Proc. of the Amer. for Cancer Res. 38, Mar. 1997, p. 94.

A. Raz et al. Endogenous galactoside–binding lectins: a new class of functional tumor cell surface molecules related to metastasis. Cancer & Metast. Rev. 6 (1987) pp. 433–452.

S. Fujimoto et al. Clinical Outcome of Postoperative Adjuvant Immunochemotherapy with Sizofiran for Patients with Resectable etc. Eur. J. Cancer 27(9), pp. 1114–1118.

C.M.G.C. Renard et al. Structure of the repeating units in the rhamnogalacturonic backbone of apple, beet and citrus pectins. Carb. Res. 275 (1995) pp. 155–165.

A.N. Round et al. Investigating the nature of branching in pectin by atomic force microscopy and carbohydrate analysis. Carb. Res. 331 (2001) pp. 337–342.

J. M. Ros et al. Extraction, characterisation, and enzymatic deradation of lemon peel pectins. Carb. Res 282 (1996), pp. 271–284.

D. Zhan et al. Scarcity or complete lack of single rhamnose residues interspersed within the homogalacturonan regions of citrus pectin. Carb. Res. 308 (1998) pp. 373–380.

Propharmaceutics, Inc. Confidential Private Placement Memorandum, Aug. 23, 2000, pp. 1–63.

Aparicio, A. "In vitro cytoreductive effectsion multiple myeloma cells induced by bisphosphonates." Leukemia 12, 220–229 (1998).

Bold, R.J. et al. "Chemosensitization of Pancreatic Cancer by Inhibition of the 26S Proteasome." J. Surg. Res. 100, 11–17 (2001).

Brewer, C.F. "Binding and cross–linking properties of galectins, Bochim. Biophys." Acta 1572, 255–262 (2002).

Burke, P.A. et al. "Combined Modality Radioimmunotherapy." Cancer 94, 1320–1331 (Feb. 15, 2002).

Camby, I. et al. "Galectins are differently expressed in supratentorial pilocytic astrocytomas, astrocytomas, anaplastic astrocytomas and glioblastomas, and significantly modulate tumor astrocyte migration." Brain Pathology 11, 12–26 (2001).

Cherayil, B.J. et al. "Molecular cloning of a human macrophage lectin specific for galactose." PNAS 87, 7324–7328 (Sep. 1990).

Choufani, G. et al. "The Levels of Expression of Galectin–1, Galectin–3, and the Thomsen–Friedenreich Antigen and Their Binding Sites Decreases as Clinical Aggressiveness Increases In Head and Neck Cancers. Cancer 86, 2353–2363 (Dec. 1, 1999)."

Cindolo, L. et al. "Galectin–1 and Galectin–3 Expression in Human Bladder Transitional–Cell Carcinomas." Int. J. Cancer 84, 39–43 (1999).

Cooper, D.N.W. "Galectinomics: finging themes in complexity." Biochim Biophys Acta 1572, 209–231 (2002).

Cotter, British Journal of Haematology 111:52–60 (2000).

Danguy, A. et al. "Galectins and cancer." Biochim. Biophys Acta 1572, 285–293 (2002).

Del Bino, G. et al. "Altered Susceptibility of Differentiating HL–60 Cells to Apoptosis Induced by Antitumor Drugs." Leukemia 8, 281–288 (Feb. 1994).

Dipaola, R.S. and Aisner, J. "Overcoming bcl–2– and p53–Mediated Resistance in Prostate Cancer." Seminars n Oncology 26, 112–116 (Feb. 1999).

Eastman, A. and Rigas, J.R. "Modulation of Apoptosis Signaling Pathways and Cell Cycle Regulation." Seminars in Oncology 26, 7–16 (Oct. 1999).

Fan, W. et al. "In vitro evaluation of combination chemotherapy against human tumor cells." Oncology Reports 5, 1035–1042 (1998).

Francois, C. et al. "Galectin–1 and Galectin–3 Binding Pattern Expression in Renal Cell Carcinomas." Am. J. Clin. Pathol. 112, 194–203 (1999).

Frankel et al. "Synthetic glycoamine analogs synergies with taxol and cisplatin in inducing programmed cell depth in ovarian cancer cells." Proc Am Assoc Can Res (1997) 88th Ann Meeting, abstr. #627.

Fujimoto et al., "Clinical Outcome of Postoperative Adjuvant Immunochemotherapy with Sizofiran for Patients with Resectable Gastric Cancer: a Randomised Controlled Study," Eur J Cancer (1991) 27(9), pp. 1114–1118.

Glinsky et al., "Inhibition of colony formation in agarose of metastatic human breast carcinoma and melanoma cells by synthetic glycoamine analogs." Clin. Exp. Metastasis (1996) 14, pp. 253–267.

Glinsky et al., "Inhibition of Human Breast Cancer Metastasis in Nude Mice by Synthetic Glycoamines." Cancer Research (1996) 56, pp. 5319–5324.

Glinsky, G.V., "Anti–adhesion cancer therapy." Cancer and Metastasis Reviews (1998) 17, pp. 177–185.

Grant, S. and Dent, P. "Rational Integration of agents directed at novel therapeutic targets into combination chemotherapeutic regiments." Curr. Opin. Investigational Drugs 2, 1600–1605 (2001).

Green et al., "Adhesion–dependent multicellular drug resistance." Anti–Cancer Drug Design (1999) 14, pp. 153–168.

Hara, I. et al. "Sodium butyrate induces apoptosis in human renal cell carcinoma cells and synergistically enhances their sensitivity to anti–Fas–mediated cytotoxicity," Int. J. Oncol. 17, 1213–1218 (2000).

Hernandez, J.D. and Baum, L.G. "Ah, sweet mystery of death! Galectins and control of cell fate." Glycobiology 12, 127R–136R (2002).

Hortobagyl, G.N. "Recent Progress in the Clinical Development of Docetaxel (Taxotere)." Seminars in Oncology 26, 32–36 (Jun. 1999).

Hrdlickova, E. et al. Detection of galectin–3 in tear fluid at disease states and immunohistochemical and lectin histochemical analysis in human corneal and conjunctival epithelium. Br. J. Ophthalmol. 85, 1336–1340 (2001).

Hua Chang Gon et al., "The NH2 Terminus of Galectin–3 Governs Cellular Compartmentalization and Functions in Cancer Cells," Cancer Research 59:6239–6245 (1999).

Huel–Min Lin et al., "Calectin–3 Mediates Genistein–induced G2/M Arrest and Inhibits Apoptosis," Carcinogenesis 21(11):1941–1945 (2000).

Hyeong–Reh Chol Kim et al., "Cell Cycle Arrest and Inhibition of Anoikis by Galectin–3 in Human Breast Epithelial Cells," Cancer Research 59:4148–4154 (1999).

Ida Iurisci et al., "Concentrations of Galectin–3 in the Sera of Normal Controls and Cancer Patients," Clinical Cancer Research 6:1389–1393 (2000).

Inohara, H. et al. "Expression of Galectin–3 in Fine–Needle Aspirates as a Diagnostic Marker Differentiating Benign from Malignant Thyroid Neoplasms." Cancer 85, 2475–2484 (Jun. 1, 1999).

Inohara, H. et al., "Effect of Natural Complex Carbohydrate (Citrus Pectin) on Muriine Melanoma Cell Properties Related to Galectin–3 Functions," Glycoconjugate Journal 11:527–532 (1994).

Inufusa, H. et al. "Role of galectin–3 adenocarcinoma liver metastasis." Int. J. Oncol. 19, 913–919 (2001).

Jensen–Jarolim, E. et al. "Anti–Galectin–3 IgG Autoantibodies in Patients with Crohn's Disease Characterized by Means of Phage Display Peptide Libraries." J. Clin. Immunol. 21(5), 348–356 (2001).

Johnson, K. R. et al. "Antagonistic Interplay between Antimitotic and G1–S Arresting Agents Observed in Experimental Combination Therapy," Clin. Cancer Res. 5, 2559–2565 (Sep. 1999).

Juliao, S. et al. "Galectin–3: A Marker and Diagnostic Aid for Chordoma." Present at the 47th Annual Meeting, Orthopaedic Research Society, Feb. 25–28, 2001, San Francisco, CA.

Karmanos, Barbara Ann Cancer Institute. "Novel Therapeutic Target & Therapies." www.karmanos.org/we/research/prostate/novel.html retrieved on Jan. 27, 2003.

Kilpatrick, D. C. "Animal Lectins: a historical introduction and overview." Biochim. et Biophys. Acta 1572, 187–197 (2002).

Kim, R. et al. "A pitfall in the survival benefit of adjustment chemotherapy for node– and hormone receptor–positive patients with breast cancer: The paradoxical role of Bcl–2 oncoprotein (Review)." Int. J. Oncol. 19, 1075–1080 (2001).

Klasa, R. J. et al. "Eradication of Human Non–Hodgkin's Lymphoma in SCID Mice by BCL–2 Antisense Oligonucleotides Combine with Low–Does Cyclophosphamide." Clin. Cancer Res. 6, 2492–2500 (Jun. 2000).

Leffler, H. et al. "Specificity of Binding of Three Soluble Rat Lung Lectins to Substituted and Unsubsituted Mammalian B–Galactosides." J. Biol. Chem. 261(22), 10119–10126 (Aug. 5, 1986).

Lim, Y. et al. "Identification of autoantibodies associated with systemic lupus erythematosus. Biochem." Biophys. Res. Comm. 295, 119–124 (2002).

Linehan, W. M. "Inhibition of Prostate Cancer Metastasis: a Critical Challenge Ahead J. Nat." Cancer Inst. 87(5), 331–332 (Mar. 1, 1995).

Liu, F.–T. et al. "Intracellular functions of galectins." Biochim et Biophys Acta 1572, 263–273 (2002).

Lopes de Menezes, D. E. et al. "Molecular and Pharmacokinetic Properties Associated with the Therapeutics of Bcl–2 Antisense Oligonucleotide G3139 Combined with Free and Liposomal Doxorubicin." Clin. Cancer Res. 6, 2891–2902 (Jul. 2002).

Lotz, M. M. et al. "Decreased expression of Mac–2 (carbohydrate binding protein 35) and loss of its nuclear localization are associated with the neoplastic progression of colon carcinoma." PNAS 90, 3466–3470 (Apr. 1993).

Majlessipour, F. "The Combination Regimen of Idarubicin and Taxotere is Effective Against Human Drug–resistant Leukemic Cell Lines." Anticancer Res. 22, 1361–1368 (2002).

Matarrese P., et al., (Abstract) "Galectin–3 Overexpression Protects from Apoptosis by Improving Cell Adhesion Properties," Int. Cancer 85(4):545–554 (2000).

Matarrese, P., et al. "Galectin–3 overexpression protects from cell damage and death by influencing mitochondrial homeostasis." FEBS Letters 473, 311–315 (2000).

Mey, A. et al. "Expression of the galactose binding protein Mac–2 by human melanoma cell–lines." Cancer Letters 81, 155–163 (1994).

Nachman Mazuret et al., "Phosphorylation of the B–Galactoside–binding Protein Galectin–3 Modulates Binding to its Ligands," The Journal of Biological Chemistry 275(46):36311–36315 (2000).

Nakamura, M. et al. "Involvement of galectin–3 expression colorectal cancer progression and metastasis." Int. J. Oncol: 15, 143–148 (1999).

Ohannesian, D. W. et al. "Carcinoembryonic Antigen and Other Glycoconjugates Act as Ligands for Galectin–3 in Human Colon Carcinoma Cells." Cancer Res. 55, 2191–2199 (May 15, 1995).

Oncolink: Lilly Oncology Treatment Options. www.oncolink.com/treatment/section.cfm retrieved on Feb. 12, 2003.

Orlandi, F. et al. "Galectin–3 is a Presurgical Marker of Human Thyroid Carcinoma." Cancer Res. 58, 3015–3020 (Jul. 15, 1998).

Pascal O. Berberat et al., "Comparative Analysis of Galectins in Primary Tumors of Tumor Metastasis in Human Pancreatic Cancer," The Journal of Histochemistry & Cytochemistry 49(4):539–549 (2001).

Perillo, N. L. "Galectins: versatile modulators of cell adhesion, cell proliferation, and cell death." J. Mol. Med. 76, 402–412 (1998).

Pienta, K.J. et al. "Inhibition of spontaneous metastasis in a rat prostate cancer model by oral administration of modified citrus pectin." J. Nat. Cancer Inst. 87(5), 348–353 (Mar. 1, 1995).

Platt, D. and Raz, A. "Modulation of the Lung Colonization of B16–F1 Melanoma Cells by Citrus Pectin." J. Nat. Cancer Inst. 84, 438–442 (Mar. 18, 1992).

Propharmaceuticals, Inc. Confidential Private Placement Memorandum, Aug. 23, 2000, pp. 1–63.

Pugliese, G. "The Diabetic Milieu Modulates the Advanced Glycation End Product–Receptor Comples in the Mesangium by Inducing or Upregulating Galectin–3 Expression." Diabetes 49, 1249–1257 (Jul. 2000).

Rabinovich G.A. et al., "Galectins and Their Ligands: Amplifiers, Silencers or Tuners of the Inflammatory Response?" Trends in Immunology 23(6):313–320 (2002).

Rabinovich, G.A. "Role of galectins in Inflammatory and immunomodulatory processes. Biochim. Biophys." Acta 1572, 274–284 (2002).

Rabinovich, G.A. et al. "Recombinant Galectin–1 and Its Genetic Delivery Suppress Collagen–Induced Arthritis via T Cell Apoptosis." J. Exp. Med. 190(3), 385–397 (Aug. 2, 1999).

Rabinovich, G.A. et al. "The antimetastatic effect of a single low dose of cycolphosphamide involves modulation of galectin–1 and Bcl–2 express," Cancer Immunol. Immunother. 50, 597–603 (2002).

Raynaud, F. I. "Pharmacokinetics of G3139, a Phosphorothioate Oligodeoxynucleotide Antisense to bcl–2, after Intravenous Administration or Continuous Subcutaneous Infusion to Mice. J. Pharmacol." Exp. Therapeutics 281(1), 420–427 (1997).

Raz A. et al., "Endogenous galactoside–binding lectins: a new class of functional tumor cell surface molecules related to metastasis." Cancer and Metastasis Reviews (1987) 6, pp. 433–452.

Renard et al., "Structure of the repeating units in the rhamnogalacturonic backbone of apple, beet and citrus pectins." Carbohydrate Research (1995) 275, pp. 155–165.

Ros, J.M., et al., "Extraction, characterisation, and enzymatic degration of lemon peel pectins." Carbohydrate Research (1996) 282, pp. 271–284.

Round et al., "Investigating the nature of branching in pectin by atomic force microscopy and carbohydrate analysis." Carbohydrate Research (2001) 331, pp. 337–342.

Rudin, C. M. et al. "A pilot trial of G3139, a bcl–2 antisense oligonucleotide, and paclitaxel in patients with chemorefractory small–cell lung cancer." Ann. Oncol. 13, 539–545 (2002).

Ruiter, G. A. et al. "Alkyl–Lysophospholipids as Anticancer Agents and Enhancers of Radiation–Induced Apoptosis." Int. J. Radiation Oncol. Biol. Phys. 49(2), 415–419 (2001).

S.E. Baldus et al., "Increased Galectin–3 Expression in Gastric Cancer: Correlations with Histopathological Subtypes, Galactosylated Antigen and Tumor Cell Proliferation," Tumor Biol., 21:258–266 (2000).

Sano, H. et al. "Human Galectin–3 is a Novel Chemoattractant for Monocytes and Macrophages." J. Immunol. 165, 2156–2164 (2000).

Sauer, G. et al. "New Molecular Targets of Breast Cancer Therapy." Strahlenther. Onkol. 178(3), 123–133 (2002).

Shih, C. et al. Cryptophycins: "A Novel Class of Potent Antimitotic Antitumor Depsipeptides." Curr. Pharm. Des. 7, 1259–1276 (2001).

Sorme, P. et al. "Low Micromolar Inhibitors of Galectin–3 Based on 3–Derivatization of N–Acetyllactosmaine." ChemBioChem 3, 183–189 (2002).

Takahashi, T. et al. "Mechanisms of the apoptotic activity of Cl–F–araA in a human T–ALL Cell line, CCRF–CEM." Cancer Chemother Pharmacol. 50, 193–201 (2002).

Tentori, L. et al. "Role of Wild–Type p 53 on the Antineoplastic Activity of Temozolomide Alone or Combined with Inhibitors of Poly(ADP–Ribose) Polymerase." J. Pharmacol. Exp. Therapeutics 285(2), 884–893 (1998).

Tortora, G. et al. "Combined Blockade of Protein Kinase A and Bcl–2 by Antisense Strategy Induces Apoptosis and Inhibits Tumor Growth and Angiogenesis." Clin. Cancer Res. 7, 2537–2544 (Aug. 2001).

Tortora, G. et al. "Protein Kinase A as Target for Novel Integrated Strategies of Cancer Therapy." Ann. N.Y. Acad. Sci. 968, 139–147 (2002).

Tu, S.–M. et al. "Combination adriamycin and suramin induces apoptosis in bcl–2 expressing prostate carcinoma cells." Cancer Letters 93, 147–155 (1995).

Usuda, J. et al. "Increased Cytotoxic Effects of Photodynamic Therapy in IL–6 Gene Transfected Cells via Enhanced Apoptosis." Int. J. Cancer 93, 475–40 (2001).

Vivat–Hannah, V. et al. "Synergistic Cytotoxicity Exhibited by Combination Treatment of Selective Retinoid Ligands with Taxol (Paclitaxel)." Cancer Res. 61(24), 8703–8711 (Dec. 15, 2001).

Vladislave V. Glinsky et al., "Effect of Thomsen–Friedenreich Antigen–specific Peptide P–30 on B–Galactoside–mediated Homotypic Aggregation Adhesion to the Endothellum of MDA–MB–435 Human Breast Carcinoma Cells," Cancer Research 60:2584–2588 (2000).

Vladislav V. Glinsky et al., "The Role of Thomsen–Friedenreich Antigen in Adhesion of human Breast and Prostate Cancer Cells to the Endothelium," Cancer Research 61:4851–4857 (2001).

Webster's New World Dictionary, 3rd. ed., Simon & Schuster (New York, 1988) p. 433.

Wen–Qin Zhu et al., "Rapin Release of Intracellular Galectin–3 from Breast Carcinoma Cells by Fetuin," Cancer Research 61:1869–1873 (2001).

Wu, X.–X. et al. "Enhancement of Fas–mediated Apoptosis in Renal Cell Carcinoma Cells by Adriamycin." Cancer Res. 60, 2912–2818 (Jun. 1, 2000).

Xia, F. "The molecular basis of radiosensitivity and chemosensitivity in the treatment of breast cancer." Semin. Radiat. Oncol. 12(4), 296–304 (2002).

Xu, X.–C. et al. "Differential expression of galectin–1 and galectin–3 in benign and malignant salivary gland neoplasms." Int. J. Oncol. 17, 271–276 (2000).

Yamamoto, D. et al. "Synergistic action of apoptosis induced by elcosapentaenoic acid and TNP–470 on human breast cancer cells." Breast Cancer Res. Treatment 55, 149–160 (1999).

Yamaoka, K. et al. "Overexpression of A β–Galactoside Binding Protein Causes Transformation of Balb3T3 Fibroblast Cells." Biochem. Biophys. Res. Comm. 179(1), 272–279 (Aug. 30, 1991).

Yamazaki, K. et al. "Simultaneous Induction of Galectin–3 Phosphorylated on Tyrosine Residue, p21 waf1/Cip1/Sdi1, and the Proliferating Cell Nuclear Antigen at a Distinctive Period of Repair of Hepatocytes Injured by CCI4." Biochem. Biophys. Res. Comm. 280, 1077–1084 (2001).

Yang, R.–Y. et al. "Expression of galectin–3 modulates T–cell growth and apoptosis." PNAS 93, 6737–6742 (Jun. 1996).

Yoshii, T. et al. "Galectin–3 Phosphorylation is Required for its Anti–Apoptotic Function and Cell Cycle Arrest." J. Biol. Chem. 277(9), 6852–6857 (Mar. 1, 2002).

Zeng, S. et al. "In Vitro Evaluation of Schedule–dependent Interactions between Docetaxel and Doxorubicin against Human Breast and Ovarian Cancer Cell." Clin. Cancer Res. 6, 3766–3773 (Sep. 2000).

Zetter, "Angiogenesis and tumor metastasis," Annu. Rv. Med. 49:407–424 (1998).

Zhan et al., "Scarity or complete lack of single rhamnose residues interspersed within the homogalacturonan regions of citrus pectin." Carbohydrate Research (1998) 308, pp. 373–380.

* cited by examiner

INTER PARTES REEXAMINATION CERTIFICATE ISSUED UNDER 35 U.S.C. 316

THE PATENT IS HEREBY AMENDED AS INDICATED BELOW.

AS A RESULT OF REEXAMINATION, IT HAS BEEN DETERMINED THAT:

Claims 1-23 are cancelled.
Other added claims 24-58 cancelled.

\* \* \* \* \*